United States Patent
Larson et al.

(10) Patent No.: US 9,072,802 B2
(45) Date of Patent: Jul. 7, 2015

(54) SYSTEMS AND METHODS FOR DISINFECTING MEDICAL INSTRUMENTS

(75) Inventors: Brian G. Larson, Alpine, UT (US); Daryl J. Tichy, Orem, UT (US)

(73) Assignee: Solutions BioMed, LLC, Orem, UT (US)

( * ) Notice: Subject to any disclaimer, the term of this patent is extended or adjusted under 35 U.S.C. 154(b) by 0 days.

(21) Appl. No.: 13/481,634

(22) Filed: May 25, 2012

(65) Prior Publication Data

US 2013/0137162 A1    May 30, 2013

Related U.S. Application Data

(60) Provisional application No. 61/490,793, filed on May 27, 2011.

(51) Int. Cl.
  *A61L 2/18*    (2006.01)
  *A01N 59/16*    (2006.01)

(52) U.S. Cl.
  CPC .. *A61L 2/18* (2013.01); *A01N 59/16* (2013.01)

(58) Field of Classification Search
  CPC .................................. B01J 19/10; A61L 2/18
  USPC ..................... 422/128, 20, 28, 292
  See application file for complete search history.

(56) References Cited

U.S. PATENT DOCUMENTS

| | | |
|---|---|---|
| 3,007,478 A | 11/1961 | Leonhardt et al. |
| 4,710,233 A | 12/1987 | Hohmann |
| 5,095,925 A | 3/1992 | Elledge et al. |
| 5,871,692 A | 2/1999 | Haire et al. |
| 7,351,684 B2 | 4/2008 | Tichy et al. |
| 7,531,080 B2 | 5/2009 | Carson et al. |
| 7,651,672 B2 | 1/2010 | Lin et al. |
| 2006/0157343 A1 | 7/2006 | Herrington |
| 2007/0100206 A1 | 5/2007 | Lin et al. |
| 2007/0154371 A1 | 7/2007 | Lin et al. |

FOREIGN PATENT DOCUMENTS

WO    WO 97/32610    9/1997

OTHER PUBLICATIONS

PCT/US12/39730; filed May 25, 2012; Solutions Biomed, LLC; international search report dated Jul. 11, 2013.

*Primary Examiner* — Sean E Conley
(74) *Attorney, Agent, or Firm* — Thorpe North & Western LLP (57) ABSTRACT

Systems and methods for disinfecting medical instruments are provided. In one embodiment, a system can include a hood to provide a clean zone, a chamber to dispose within the clean zone, and an ultrasonicator. More specifically, the chamber can include a volume and can be configured to retain a fluid and receive medical instruments. The chamber can also include a portal through which fluids enter or leave the chamber. The ultrasonicator can be used to sonicate the volume when the fluid is present. A related method of disinfecting medical instruments can be accomplished using the systems of the present disclosure.

68 Claims, 3 Drawing Sheets

FIG. 3

SYSTEMS AND METHODS FOR DISINFECTING MEDICAL INSTRUMENTS

This application claims the benefit of U.S. Provisional Patent Application No. 61/490,793, filed May 27, 2011.

BACKGROUND

The use of sterile instruments is typically desirable for the operation of a viable medical or dental practice. Unfortunately, the disinfectant or sterilization processes available are often time consuming, labor intensive, costly, and can result in undesirable or hazardous waste. Additionally, some sterilization process can damage medical and dental equipment over a period of time. Typically, the sterilization process includes multiple steps where there is direct involvement of a technician. Such processes can also take several hours to complete. Furthermore, the lengthy duration and frequency of these sterilization techniques usually forces medical or dental providers to have large inventories of medical instruments in order to provide continuous uninterrupted service to their patients. In light of this, research continues in an effort to find fast effective sterilization techniques that are require minimal labor and are cost effective.

SUMMARY OF THE INVENTION

The present disclosure sets forth systems and methods for disinfecting medical instruments. One system includes a hood that is configured to provide a clean zone. Within the hood, a chamber can be disposed that has a volume and is configured to retain a fluid and receive medical instruments. The chamber can include a portal through which fluids enter or leave the chamber. The system further includes an ultrasonicator component. The ultrasonicator component is configured to sonicate into the volume of the chamber.

In another embodiment, a system of disinfectant medical instruments includes a chamber that has a volume and is configured to retain a fluid and receive medical instruments. The chamber further includes a portal through which fluids enter or leave the chamber. The system includes an ultrasonicator component configured to sonicate into the volume of the chamber. The system further includes a disinfectant fluid including water, a colloidal transition metal, and a peroxygen compound which can be added to the chamber for sonication.

In an additional embodiment, a method of disinfecting medical instruments is provided. The method includes the steps of providing a volume of disinfectant fluid including water, a peroxygen, and colloidal metal particles; submerging medical instruments into the disinfectant fluid; and sonicating the disinfectant fluid and medical instruments. The methods of the present disclosure can be accomplished using the disclosed disinfecting systems. The systems of the present disclosure can be configured such that the method of disinfecting can be accomplished within a time period of 60 minutes or less. In one embodiment, the disinfection can be accomplished in a time period of 30 minutes or less. In yet another embodiment, the disinfection can be accomplished in a time period of 20 minutes or less.

BRIEF DESCRIPTION OF THE DRAWINGS

Additional features and advantages of the disclosure will be apparent from the detailed description which follows, taken in conjunction with the accompanying drawings, which together illustrate, by way of example, features of the disclosure; and, wherein.

DETAILED DESCRIPTION

Reference will now be made to the exemplary embodiments, and specific language will be used herein to describe the same. It will nevertheless be understood that no limitation of the scope of the disclosure is thereby intended. Alterations and further modifications of the inventive features illustrated herein, and additional applications of the principles of the disclosures as illustrated herein, which would occur to one skilled in the relevant art and having possession of this disclosure, are to be considered within the present scope. It is also to be understood that the terminology used herein is used for the purpose of describing particular embodiments only. The terms are not intended to be limiting unless specified as such.

It must be noted that, as used in this specification and the appended claims, the singular forms "a," "an," and "the" include plural referents unless the content clearly dictates otherwise.

The use of the term "disinfect," "disinfecting," "disinfection," or the like, is used to include not only fighting infection of virus, bacteria, or other living organisms that may contaminate an item, e.g. a medical or dental instrument, but also includes decontamination of surfaces that are exposed to harmful or irritating chemicals that may be used in a medical or dental environment. Complete sterilization is not required for disinfection to occur. Generally, though disinfectant solutions are used for the same purpose, i.e. to kill bacteria and/or viruses, etc., a sterilant composition typically exhibits a greater kill level compared to a disinfectant. This being stated, most applications require only disinfectant levels of bacteria/virus reduction, though other applications benefit considerably from the use of sterilants. For convenience, in the present application the term "disinfectant" is used generally to refer to each of disinfectants and sterilants unless the context clearly dictates otherwise. In other words, disinfectant fluids or compositions taught herein can also be sterilants. Thus, in each instance the term "disinfectant" or the like is used, that term should be read to be inclusive of the term "sterilant" or other similar variant of this term, i.e. at least a disinfectant. However, if the term "sterilant," "sterilization," "sterilize" or the like is used, it is intended to mean greater level of kill associated with this term that is greater than that provided by a "disinfectant."

The term "solution" is also used throughout the specification to describe the liquid compositions. However, as these "solutions" can include colloidal transition metals or other particles and can also be described as dispersions or suspensions. As the continuous phase is typically a solution and the transition metal is present as a colloid, for convenience, these compositions will typically be referred to as "solutions" herein.

As used herein, the term "colloidal" metal refers to metal particles that are in their elemental state and does not include salts or complexes. Ionic metals may also be present when colloidal metals are present, but when referring to colloidal metals, it is understood to include at least a portion of the metal in its elemental form. Alloys are considered to be in their elemental form.

The term "substantially free" when used with regard to the compositions of the present disclosure refers to the total absence of or near total absence of a specific compound or composition. For example, when a composition is said to be substantially free of aldehydes, there are either no aldehydes in the composition or only trace amounts of aldehydes in the composition.

The term "peroxygen" refers to any compound containing a dioxygen (O—O) bond. Dioxygen bonds, particularly bivalent O—O bonds, are readily cleavable thereby allowing compounds containing them to act as powerful oxidizers. Non-limiting examples of classes of peroxygen compounds include peracids, peracid salts, and peroxides, such as hydrogen peroxide.

As used herein, the term "medical instrument" refers to both medical and dental instruments, and in particular, those instruments where it is desirable to implement disinfection/sterilization prior to their use. Non-limiting examples of medical instruments include all types of reusable surgical and dental instruments. Examples of dental instruments include, but are not limited to explorers, sickle probes, periodontal probes, straight probes, retractors, dental mirrors, bits, and the like. Example of surgical instruments include, but are not limited to forceps, other graspers, clamps, retractors, distractors, trocars, drill bits, lancets, scalpels, dilators, suction instruments, staplers, calipers, rules, endoscopes, drills, etc. These lists are not limiting, but rather, are merely exemplary of the types of instruments that can be disinfected or sterilized in accordance with embodiments of the present disclosure.

As used herein, the term "clean zone" refers to a region or volume of space created by a hood that is isolated or substantially isolated from the external environment. Once disinfected or sterilized, the clean zone remains substantially sterile due to its isolation or substantial isolation from the external environment. A clean zone can be maintained by physical walls, air flow, a combination of both, or the like.

Concentrations, dimensions, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a weight ratio range of about 1 wt % to about 20 wt % should be interpreted to include not only the explicitly recited limits of 1 wt % and about 20 wt %, but also to include individual weights such as 2 wt %, 11 wt %, 14 wt %, and sub-ranges such as 10 wt % to 20 wt %, 5 wt % to 15 wt %, etc.

In accordance with this, the present disclosure sets forth systems and methods for disinfecting medical instruments. One system includes a hood that is configured to provide a clean zone. Within the hood, a chamber can be disposed that has a volume and is configured to retain a fluid and receive medical instruments. The chamber can include a portal through which fluids enter or leave the chamber. The system further includes an ultrasonicator component. The ultrasonicator component is configured to sonicate into the volume of the chamber.

In another embodiment, a system of disinfectant medical instruments includes a chamber that has a volume and is configured to retain a fluid and receive medical instruments. The chamber further includes a portal through which fluids enter or leave the chamber. The system includes an ultrasonicator component configured to sonicate into the volume of the chamber. The system further includes a disinfectant fluid including water, a colloidal transition metal, and a peroxygen compound, which can be added to the chamber for sonication.

The disinfectant systems of the present disclosure provide the advantages of providing high quality disinfection/sterilization while reducing the costs and time associated with traditional disinfection systems and techniques. In particular, the systems of the present disclosure reduce the amount of activity that a lab technician must invest to perform the disinfection. This time savings reduces the overhead for the user (e.g. dental office, medical office, surgery center, etc.).

Figure 1:
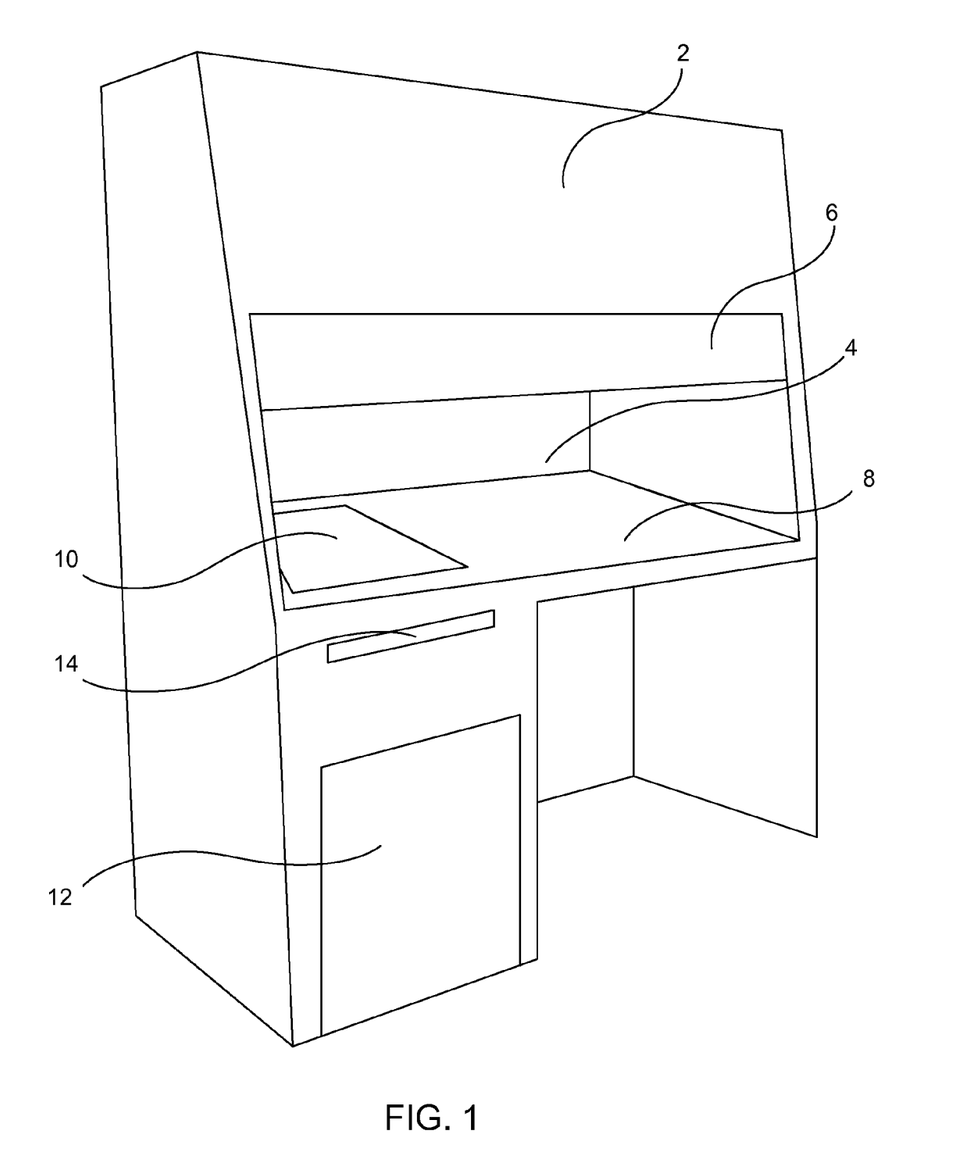
FIG. 1 is a front perspective view of an embodiment of a system of the present disclosure.

FIG. 1 shows one embodiment of a system of the present disclosure. The system includes a hood 2 that is configured to create or partially define a clean zone 4. As outlined in the above definitions, the term clean zone refers to a region or volume of space that is substantially isolated from the external environment due to the function of the hood. The term "external environment" refers to space that is outside the clean zone. In one embodiment, the clean zone can be sufficiently large to substantially enclose the chamber 10 as well as a preparation area 8. The preparation area can be used to package sterile medical instruments following their disinfection/sterilization in the chamber. The ability of a technician to package the sterilized instruments within the clean zone is advantageous because it significantly reduces the possibility of post disinfection contamination of the instruments.

The hood 2 can utilize technology including traditional exhaust hood technology, as well as the formation of an air barrier through the use of vertical or horizontal laminar air flow, which can be used to create a barrier across the front opening of the hood. In one embodiment, the air that is used to create the barrier can be filtered so that it will not contaminate or substantially contaminate the clean zone. The system can also include a door 6 that is configured to open and close across a front opening of the system. This door can be used alone or in combination with a laminar air flow barrier. FIG. 1 also shows the hood integrated with the chamber 10 as a single stand-alone system. Such an embodiment is simply exemplary of various embodiments that can be used. For example, the hood could be a separate and independent structural component from the chamber, and the chamber could be configured for portability independent of the hood. The chamber itself can have various configurations depending on the nature of the disinfection desired and the types of instruments being disinfected.

Figure 2:
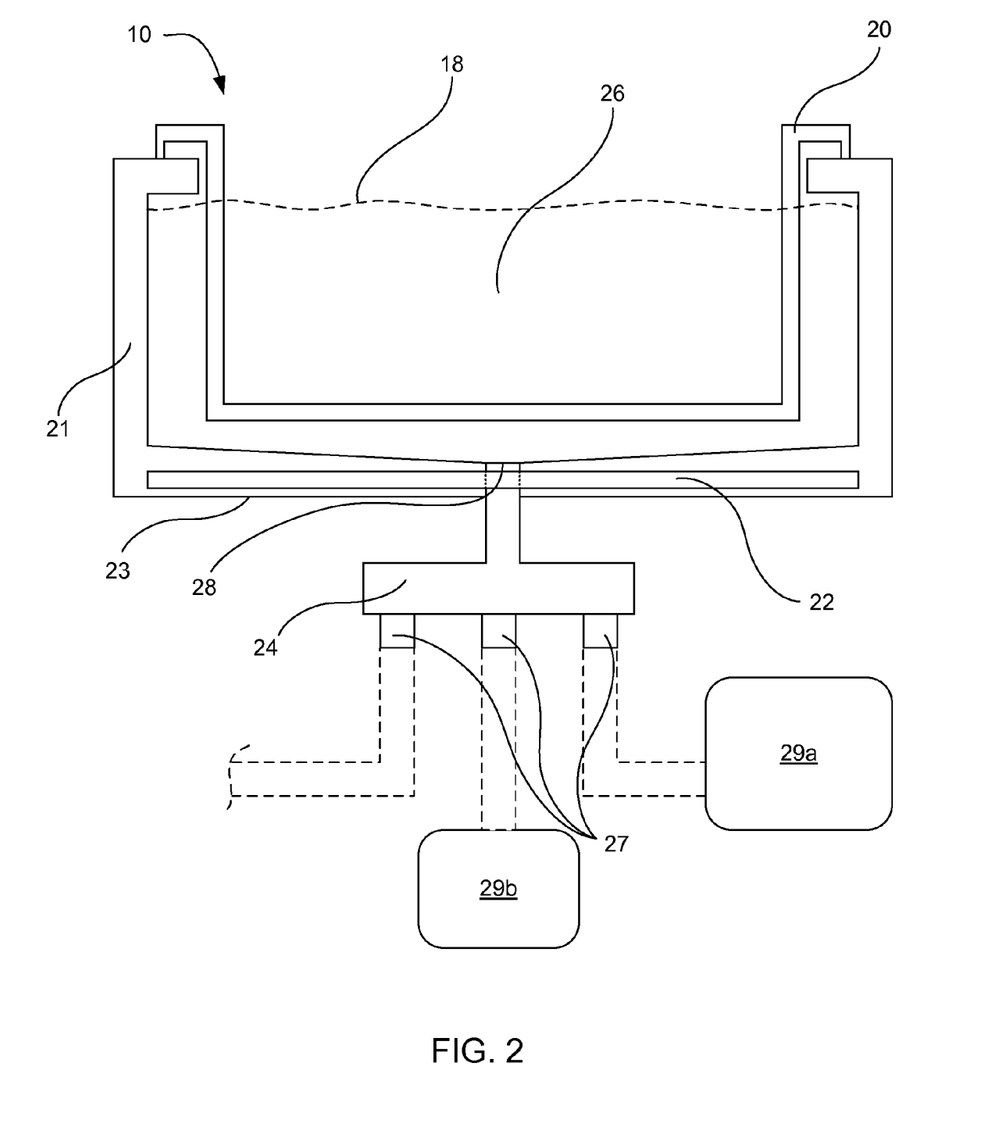
FIG. 2 is a perspective view of an embodiment of a chamber for use in the systems of the present disclosure.

FIG. 2 shows an embodiment of a chamber 10 that can be used in the systems of the present disclosure. The chamber can be a structure that defines a volume 26 into which medical instruments (not shown) may be placed for disinfection, or sterilization. The chamber can include a portal 28 configured to allow fluids to enter or leave the chamber. In one embodiment, the portal can act as the single location for both the entrance and exiting of fluids form the chamber. In another embodiment, the chamber can include multiple portals such as a drain portal and one or more inlet portals. The portal can be operably connected to one or more fluid source 29a, 29b, including a source for a disinfectant fluid. The source of the disinfectant fluid can be a fluid tank or other source such as a deionized or clean water system.

Also shown in FIG. 2, the portal 28 can be operably connected to a manifold 24 that is configured to facilitate control of fluid flow into and out of the chamber. The manifold can be operably connected to multiple fluid sources such as one or more disinfectant fluid sources as well as a rinse fluid. The manifold can also be connected to a receptacle for receiving discharged fluids after use. While the manifold shown in FIG. 2 is shown as having three connecting valves 27 (one fluidly connected to tank 29a, one fluidly connected to tank 29b, and one fluidly coupled to a line that could connect any of a number of sources such as a water line), the manifold may have a different number of connecting valves. Further, it is noted that the portal and manifold may be located on the underside of the chamber, such as shown in FIG. 2, or it may also be located along the side-walls 21 of the chamber or other appropriate location. A filter may be disposed between the portal of the chamber and the sources of fluids and/or the receptacle for discharged fluids in order to prevent the transport of or contamination by solid particles from the chamber. The filter can be configured to render the discharge fluids safe for disposal into community sewer systems without the need of special treatment.

FIG. 2 also shows an ultrasonicator 22 that is integrated with the chamber. The ultrasonicator can be disposed along the bottom wall 23 of the chamber 10, along side walls 21, or both. Any ultrasonication technology known in the art can be used in the system so long as the ultrasonicator unit can sonicate the fluid and the medical instruments that are disposed within the chamber. The embodiment of FIG. 2 also shows a basket 20 disposed within the chamber to retain the medical instruments during the disinfection or sterilization process. The basket can be made of any material known in the art, such as plastic, metal, or cloth, and should allow for free flow of the fluids 18 in the chamber so that the fluids can readily contact the medical instruments present in the basket. Although not a necessary component, the basket can act to facilitate the placement and removal of instruments to and from the chamber. The basket can be divided into various compartments or take on various configurations depending on the nature and size of the medical instruments being disinfected.

Figure 3:
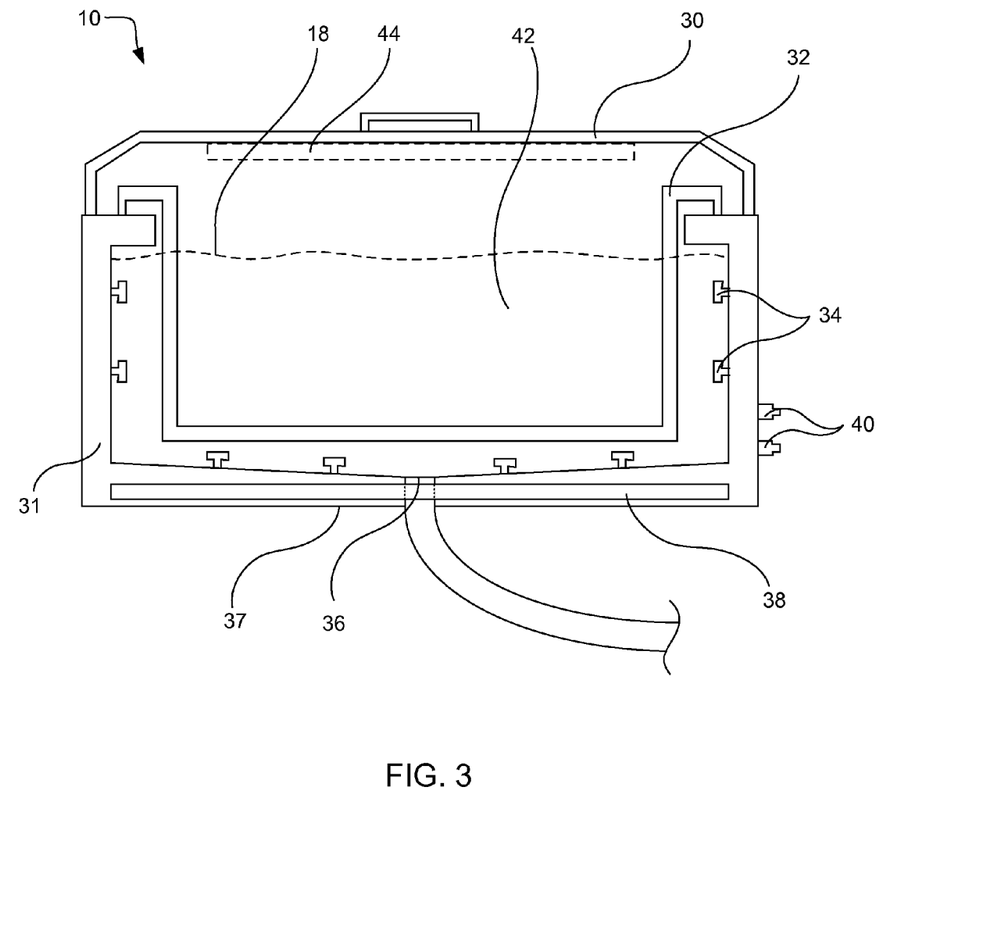
FIG. 3 is a perspective view of an additional embodiment of a chamber for use in the systems of the present disclosure.

FIG. 3 shows an additional embodiment of a chamber 10 that can be used in the systems of the present disclosure. Like the chamber of FIG. 2, the chamber includes side-walls 31 and a bottom wall 37 as well as an ultrasonicator 38 and a bottom portal 36. A basket 32 for receiving medical instruments is also shown. The chamber in FIG. 3 also shows a lid 30 which can be included in the system to cover the chamber during the disinfection process. The lid can take on any configuration and is not limited to the configuration shown in FIG. 3. The chamber in FIG. 3 also includes spray nozzles 34 located on the interior surfaces of the chamber. While shown as being present along all surfaces of the chamber, when present, such spray nozzles can be located on one or more of the side walls and/or the bottom wall. In some embodiments, the spray nozzles can also be integrated into the lid of the chamber (not shown). The spray nozzles can be operably connected with one or more portals of the chamber, and thereby, to one or more sources of fluids, including disinfectant fluid and or rinse fluid. In the embodiment shown in FIG. 3, the chamber also includes two inlet portals 40 along the exterior side of the chamber. These portals could be connected to fluid sources and can be configured to provide fluid to the spray nozzles during the disinfectant process, or for filling the chamber for sonication.

When the system is integrated as a single unit, such as in FIG. 1, or when the system is modular, in either case, a computer processing unit (CPU) 14 may also be incorporated into the system. The computer processing unit can include any processing components known in the art and can be configured to regulate flow of fluids into and out of the chamber. The regulation of fluid flow both into and out of the chamber can be accomplished through actuation of solenoids or other actuatable valves that are present within the manifold or other areas of the system. The CPU can also function to activate the ultrasonicating component of the system, or when a hood is present, can control the hood in some embodiments. The CPU can be programmable and configured to have multiple programming settings. In one aspect of the disclosure, the computer processing unit can be operably connected to sensing or monitoring equipment that monitor the potency and/or disinfective effectiveness of the system fluids. Thus, the computer processing unit can be configured to monitor the system fluids.

As outlined above, the systems of the present disclosure provide the benefit of reducing the amount of labor associated with disinfecting medical instruments. The computer processing unit facilitates this reduction in lab technician time because it allows for multiple cycles or steps of the disinfection process to occur during the process without the need for additional human labor. For example, once a technician disposes the medical instruments within the chamber, the technician can activate the system, designate the disinfection program, and walk away without the need to perform additional intervening steps. The computer processing unit could then fill and empty the disinfection chamber as well as activate the ultrasonicator unit the manner prescribed by the selected program.

It is also noted that the systems disclosed herein can also include a drying component or dryer 44 configured to accelerate the drying of the medical instruments after disinfection. The dryer can be integrated into the chamber or can be a stand-alone component of the system. When the dryer is independent of the chamber, it can be desirable to locate it within the hood so that the drying of the medical instruments can occur within the clean zone provided by the hood. The dryer can accelerate the drying of the medical instruments through any manner known in the art, so long as it maintains the disinfection of the instruments. In one embodiment, the dryer can include a heater. In another embodiment, the dryer can include a fan. Chemical dryers or desiccants may also be used.

The systems and methods of the present disclosure can use various disinfectant fluids. Examples of such disinfecting fluids include, but are not limited to enzymatic fluids, such as those discussed in the examples below, or other enzymatic digesting fluids known in the art. Another disinfectant fluid that can be used in the systems and methods of the present disclosure includes water, a peroxygen, and colloidal metal particles. In such compositions, the colloidal metal particles can be present at concentrations of about 0.001 ppm to 50,000 ppm by weight based on the aqueous vehicle content. The concentration of the colloidal metal content can be modified to 10 ppm by weight at the lower end of the range, and/or to 20,000 ppm or 10,000 ppm by weight at the upper end of the range.

In one specific embodiment, the colloidal metal can be in a sub-micron form (i.e. dispersion of less than 1 µm metal colloidal particles). However, larger colloidal transition metal particles can also be used in certain applications. Typical colloidal metals that are desirable for use include Group VI to Group XI transition metals, and more preferably, can include Group X to Group XI transition metals. Alloys including at least one metal from the Group VI to Group XI metals can also be used. It is recognized that any of these metals will typically be oxidized to the corresponding cation in the presence of a peroxygen. However, with colloidal metals, typically, the surface is usually more susceptible to such oxidation. Further, when colloidal metals are dispersed in a colloidal solution, there is often an amount of the metal in ionic or salt form that is also present in the suspension solution. For example, colloidal silver may include a certain percentage of a silver salt or ionic silver in solution. However, there will be a significant percentage of elemental colloidal metal particles. Metals for use in accordance with embodiments of the present disclosure are ruthenium, rhodium, osmium, iridium, palladium, platinum, copper, gold, silver, alloys thereof, and mixtures thereof. Silver is often used, depending on the application, and provides acceptable levels of kill that are often desired. However, other metals may be used as well, depending on the type of pathogen being targeted, the substrate that is being cleaned, etc. Any of these embodiments can also benefit from the use of alloys, where such alloys are elemental alloys in the form of colloidal particles. Examples of transition metal alloys for use in the present disclosure include, but are not limited to, copper-silver alloys, silver-manganese alloys, iron-copper alloys, chromium-silver alloys, gold-silver alloys, and magnesium-silver alloys.

Exemplary colloidal silvers that can be used include those sold by Solutions IE, Inc. under the trade names CS Plus and CS Ultra. Other colloidal silver products that can be used as the silver source include ASAP, Sovereign Silver, Silver Max, and the like. In one embodiment, the colloidal particles used in the present disclosure can have a particle size range of from 0.001 µm to 1.0 µm. In another embodiment, the colloidal metal particles can have a size range of from 0.030 µm to 0.5 µm. In still another embodiment, the average particle size is 0.35 µm to 0.45 µm. Though any colloidal silver solution that is functional for use in the formulations of the present disclosure can be used, in one embodiment, it can be desirable to use RO water as the suspension medium for the colloidal silver that is mixed with the other ingredients. In a more detailed aspect, the RO water can also be distilled, resulting in 18-20 MΩ water, though this is not required.

The peroxygen portion of the disinfectant formulation can range from about 0.001 wt % to about 40.0 wt %. In one embodiment, the range can be from 0.05 wt % to 30.0 wt %. In another embodiment, the range can be from 0.1 to 20 wt %. In yet another embodiment, the range can be from 0.5 wt % to 10 wt %. In yet another embodiment, the peroxygen can be any aliphatic or aromatic peracid (or peroxyacid) that is functional for disinfectant purposes in accordance with embodiments of the present disclosure. While any peroxyacid could be used, peroxyacids containing from 1 to 7 carbons are the most practical for use. These peroxyacids can include, but not be limited to, peroxyformic acid, peroxyacetic acid, peroxyoxalic acid, peroxypropanoic acid, perlactic acid, peroxybutanoic acid, peroxypentanoic acid, peroxyhexanoic acid, peroxyadipic acid, peroxycitric, and/or peroxybenzoic acid and mixtures thereof. The peroxyacid used in the present disclosure can be prepared using any method known in the art. When the peroxyacid is prepared from an acid and hydrogen peroxide, the resultant mixture contains both the peroxyacid and the corresponding acid that it is prepared from. For example, in embodiments that utilize peroxyacetic acid, the presence of the related acid (acetic acid) provides stability to the mixture, as the reaction is an equilibrium between the acid, hydrogen peroxide, and the peroxyacid and water, as follows:

$$H_2O_2 + CH_3COOH \rightleftharpoons CH_3COO-OH + H_2O$$

Peracid salts, such as salts of the above listed peracids, can also be included in peroxygen component of the disinfectant solutions. Non-limiting examples of such salts include permanganates, perborates, perchlorates, peracetates, percarbonates, persulphates, and the like. The salts can be used alone or in combination with each other or other peroxygen compounds to form the peroxygen component of the present disclosure.

In another embodiment, the peroxygen component of the disclosure can include a peroxide compound. While hydrogen peroxide is considered to be desirable peroxide for use in accordance with embodiments of the present disclosure, other peroxides can also be used, such as metal peroxides and peroxyhydrates. The metal peroxides that can be used include, but are not limited to, sodium peroxide, magnesium peroxide, calcium peroxide, barium peroxide, and/or strontium peroxide. Other salts (for example sodium percarbonate) have hydrogen peroxide associated therewith much like waters of hydration, and these could also be considered to be a source of hydrogen peroxide, thereby producing hydrogen peroxide in situ. Generally, when peroxides are used in the peroxygen component of the present disclosure they are used in combination with other non-peroxide peroxygen compounds, e.g. peracids.

The above described disinfectant fluid can also include other ingredients including organic co-solvents. In particular, certain alcohols can be present. It is noted that if an alcohol is present, it can be present at from 0.05 wt % to 40 wt %, with the lower end of the range of the alcohol being modifiable to 0.05 wt % or 0.1 wt %, and the upper end of the range being modifiable to 20 wt % or 10 wt %. In selecting the type of alcohol that can be used, for example, alcohols, including aliphatic alcohols and other carbon-containing alcohols, having from 1 to 24 carbons ($C_1$-$C_{24}$ alcohol) can be used. It is to be noted that "$C_1$-$C_{24}$ alcohol" does not necessarily imply only straight chain saturated aliphatic alcohols, as other carbon-containing alcohols can also be used within this definition, including branched aliphatic alcohols, alicyclic alcohols, aromatic alcohols, unsaturated alcohols, as well as substituted aliphatic, alicyclic, aromatic, and unsaturated alcohols, etc. In one embodiment, the aliphatic alcohols can be $C_1$ to $C_5$ alcohols including methanol, ethanol, propanol and isopropanol, butanols, and pentanols, due to their availability and lower boiling points. This being stated, polyhydric alcohols can also be used effectively in enhancing the disinfectant and sterilant potency of the compositions of the present disclosure, as well as provide some degree of added stabilization. Examples of polyhydric alcohols which can be used in the present disclosure include but are not limited to ethylene glycol (ethane-1,2-diol) glycerin (or glycerol, propane-1,2,3-triol), and propane-1,2-diol. Other non-aliphatic alcohols may also be used including but not limited to phenols and substituted phenols, erucyl alcohol, ricinolyl alcohol, arachidyl alcohol, capryl alcohol, capric alcohol, behenyl alcohol, lauryl alcohol (1-dodecanol), myristyl alcohol (1-tetradecanol), cetyl (or palmityl) alcohol (1-hexadecanol), stearyl alcohol (1-octadecanol), isostearyl alcohol, oleyl alcohol (cis-9-octadecen-1-ol), palmitoleyl alcohol, linoleyl alcohol (9Z,12Z-octadecadien-1-ol), elaidyl alcohol (9E-octadecen-1-ol), elaidolinoleyl alcohol (9E,12E-octadecadien-1-ol), linolenyl alcohol (9Z,12Z,15Z-octadecatrien-1-ol), elaidolinolenyl alcohol (9E,12E,15-E-octadecatrien-1-ol), combinations thereof and the like.

In some embodiments, for practical considerations, methanol, ethanol, and denatured alcohols (mixtures of ethanol and smaller amounts of methanol, and optionally, minute amounts of benzene, ketones, acetates, etc.) can often be used because of their availability and cost. Glycerol is also a good option for use in some embodiments. If the desire is to provide a food grade composition, then alcohols can be selected that satisfy this requirement. As these ranges are merely exemplary, one skilled in the art could modify these ranges for a particular application, considering such things as whether alcohol selected for use is polyhydric, whether the alcohol is food grade, mixtures of alcohols, etc.

The systems of the present disclosure can be configured to be independent free-standing systems that are portable and do not require external connections. This allows the systems to be used in all types of situations, such as in field hospitals. In one embodiment of the disclosure, the system can include a power generator configured to provide power to the system. In another embodiment, the power generator is a solar cell. In another embodiment, the power generator is a gas-powered generator.

In an additional embodiment, a method of disinfecting medical instruments is provided. The method includes the steps of providing a volume of disinfectant fluid including water, a peroxygen, and colloidal metal particles; submerging medical instruments into the disinfectant fluid; and sonicating the disinfectant fluid and medical instruments. The methods of the present disclosure can be accomplished using the disclosed disinfecting systems. The systems of the present disclosure can be configured such that the method of disinfecting can be accomplished within a time period of 60 minutes or less. In one embodiment, the disinfection can be accomplished in a time period of 30 minutes or less. In yet another embodiment, the disinfection can be accomplished in a time period of 20 minutes or less.

The disinfectant fluid of the method of the present disclosure can be disposed in a chamber, such as one of the systems described herein. The chamber can be configured to receive the disinfectant fluid and the medical instruments. The medical instruments can be disposed directly into the fluid in the chamber or they can be disposed in an instrument basket prior to being submerged in the disinfectant fluid. The placement of the instruments in a basket or carrier allows for ease of handling following disinfection.

In addition to sonication in the disinfectant fluid containing a peroxygen, water and colloidal metal, the disinfectant methods of the present disclosure can further include the step of sonication of the medical instruments in a second disinfectant fluid. Typically, this sonication step occurs prior to the sonication of the medical instruments in the first disinfectant fluid. The second disinfectant fluid can be an enzymatic fluid or a detergent type fluid that helps loosen particles and films from the surfaces of the medical instruments.

The method can also further comprise the step of rinsing the medical instruments after sonication in the disinfectant fluid or the second disinfectant fluid. The rinse can be with water, ethanol, isopropyl alcohol, or another rinse fluid. The medical instruments can also be dried following sterilization. As discussed above, the drying can be accomplished through air flow, such as a fan, heat, or a combination thereof.

EXAMPLE

Ultra-Sonication Disinfectant Fluid Synergy

A study was conducted to determine the antimicrobial activity of a disinfectant containing a water, peroxygen, and colloidal metal particles when used in combination with ultrasonication on carriers coated with spores from *Bacillus subtilis*. The test carriers were porcelain rings that were coated with *Bacillus subtilis* ATCC 19659 spores that were purchased from Presque Isle. The original solution, approximately $1 \times 10^9$ cfu/mL, was diluted 1:80 (V/V) in sterile water to achieve spore loads of $1.0 \times 10^6$ to $1 \times 10^6$ per carrier. Carriers were placed in the diluted spore suspension described above for 10 minutes and then air dried for 30 minutes. After the air dry, the carriers were dried under vacuum for 24 hours.

The ultrasonic device used in the test was a new BioSonic UC300 by Whaledent. A comparative cleaning solution was Enzymatic Ultrasonic Cleaner by BioSonic, Lot number 10028, Exp. 12/11, which was diluted according to the manufacturers' directions (1:128).

The testing was accomplished by precleaning with an enzymatic solution and then with the peroxygen, water, and colloidal metal disinfectant fluid. Ten of the coated porcelain rings were individually placed in 10 ml tubes containing the diluted enzymatic ultrasonic cleaner described above. The tubes in the enzymatic solution were sonicated for 5 minutes. The enzymatic solution was then removed from the tubes and replaced with 10 ml of a disinfectant fluid including a peroxygen, water, and colloidal metal particles (colloidal silver). The tubes were again sonicated for 5 minutes. Following sonication, the porcelain carriers were placed in 10 ml of Fluid Thioglycollate Medium (FTM) in a primary tube, then gently mixed and moved to a secondary tube of FTM. Both the primary and secondary tubes were incubated at 37° C. for 21 days.

Several controls were prepared along with the test samples. Duplicate samples of 1 ml were taken from three tubes containing the used enzymatic cleaner following the sonication. The samples were filtered using Millipore Manifold filtration systems and the filters were rinsed with about 100 ml of sterile physiological saline solution (PSS) and the membranes removed to Columbia agar plates. The agar plates were incubated at 37° C. for about 24 hours. Similarly, duplicate samples of unused disinfectant fluid and the physiological saline solution were filtered in the same manner, then plated and incubated. Sterility controls for the Columbia agar, FTM, PSS, and Tween rinse were also performed.

The spore load on the test carriers was determined by exposing five carriers to the following treatment: Sonication for 5 minutes in separate tubes containing 10 mL of 1% Tween 80, followed by vortexing for 2 minutes to remove spores from the carriers. This solution was then diluted and plated in duplicate to quantify the spore load.

The results are provided as follows:

Table 1a—Spore Coated carriers exposed to 5 minute enzymatic precleaning by sonication in enzymatic solution, followed by 5 minute sonication in the disinfectant solution. Tubes were incubated for 3 weeks at 37° C.

| Tube # | Primary | Secondary |
|---|---|---|
| 1 | − | − |
| 2 | − | − |
| 3 | − | − |
| 4 | − | − |
| 5 | − | − |
| 6 | − | − |
| 7 | − | − |
| 8 | − | − |
| 9 | − | − |
| 10 | − | − |

TABLE 1b

Enzymatic Cleaner Spore Removal Control

| Tube # | Dilution | Counts |
|---|---|---|
| 1 | $10^0$ | TNC* |
| 1 | $10^{-1}$ | TNC* |
| 4 | $10^0$ | TNC* |
| 4 | $10^{-1}$ | TNC* |
| 9 | $10^0$ | TNC* |
| 9 | $10^{-1}$ | TNC* |

TABLE 1b-continued

Enzymatic Cleaner Spore Removal Control

| Tube # | Dilution | Counts |
|---|---|---|

*TNC—Too Numerous to Count

TABLE 1c

Inoculated Carrier Positive Controls

| Tube # | Primary | Secondary |
|---|---|---|
| 1 | + | + |
| 2 | + | + |

TABLE 1d

Sterility Controls

| Material | Growth |
|---|---|
| Physiological Saline Solution | − |
| Disinfectant Fluid | − |
| Enzymatic Cleaner | + (1 colony) |
| Tween Rinse | − |
| Columbia agar | − |

As can be seen from the Table above, the sterility controls showed no growth in any of the solutions or media used, except for the enzymatic cleaner which showed one cfu. This is to be expected since the cleaner is not a sterile solution.

TABLE 1e

Spore Load Determination of Untreated Carriers

| Carrier Number | CFU/ML from Dilution $1.1 \times 10^3$ | CFU/ML from Dilution $1.1 \times 10^4$ | Number of spores/carrier |
|---|---|---|---|
| 1 | 70 | 5 | $6.55 \times 10^5$ |
| 1 | 61 | 5 | |
| 2 | 36 | 3 | $3.70 \times 10^5$ |
| 2 | 38 | 5 | |
| 3 | 15 | 4 | $1.25 \times 10^5$ |
| 3 | 10 | 0 | |
| 4 | 21 | 4 | $2.15 \times 10^5$ |
| 4 | 22 | 3 | |
| 5 | 5 | 1 | $5.50 \times 10^5$ |
| 5 | 6 | 2 | |

Mean number of spores/carrier = $2.84 \times 10^5$

Results of the testing showed that when carriers were subjected to the pre-cleaning described above (5 minutes of sonication in the enzymatic cleaner) followed by minutes of sonication in the disinfectant fluid, no viable spores remained on any of the porcelain carriers. Since the average load on these carriers was at least $2.84 \times 10^5$ spores, this dual treatment resulted in greater than a 5.45 log reduction of dried *B. subtilis* spores. A significant number of spores were removed by the pre-cleaning as evidenced from the place counts in Table B above. A 1-ml sample from the 1:10 dilution of the enzymatic cleaner showed TNC indicating more than 500 cfu. This would translate into a removal of several thousand spores from theses carriers. It can be concluded that the above disinfectant method is sufficient to render contaminated instruments sterile.

While the forgoing examples are illustrative of the principles of the present disclosure in one or more particular applications, it will be apparent to those of ordinary skill in the art that numerous modifications in form, usage and details of implementation can be made without the exercise of inventive faculty, and without departing from the principles and concepts of the disclosure. Accordingly, it is not intended that the disclosure be limited, except as by the claims set forth below.

What is claimed is:

1. A system for disinfecting medical instruments, comprising:
    a laminar flow hood to provide a clean zone that encloses a preparation area and a chamber with an ultrasonicator;
    wherein air is filtered in the clean zone to prevent contamination of the clean zone which is maintained by physical walls, filtered air flow, or a combination of both;
    wherein the preparation area is disposed within the clean zone, and wherein the clean zone is adapted to be in isolation from contamination by an external environment during use of the preparation area;
    wherein the chamber is disposed within the clean zone, said chamber having a volume and being configured to retain a fluid and receive medical instruments, the chamber including a portal through which fluids enter or leave the chamber; and
    wherein the ultrasonicator is used to sonicate into the volume of the chamber when the fluid is present.

2. The system of claim 1, wherein the portal is operably connected to a source of a disinfectant fluid.

3. The system of claim 2, wherein the disinfectant fluid is an aqueous fluid and includes at least two of hydrogen peroxide, a peracid, an alcohol, and colloidal metal particles.

4. The system of claim 2, wherein the source of the disinfectant fluid is a disinfectant fluid tank.

5. The system of claim 2, wherein the source of disinfectant fluid includes at least two disinfectant fluids.

6. The system of claim 2, wherein the source of the disinfectant fluid is an enzyme or detergent solution.

7. The system of claim 2, wherein the disinfectant fluid is an aqueous fluid and includes a peroxygen and colloidal silver particles.

8. The system of claim 7, wherein the peroxygen includes a peroxide.

9. The system of claim 7, wherein the peroxygen includes both a peroxide and a peracid.

10. The system of claim 1, wherein the portal is operably connected to a source of a rinse fluid.

11. The system of claim 10, wherein the rinse fluid is water.

12. The system of claim 1, wherein the portal is operably connected to a manifold configured to control inlet and outlet of fluids from the chamber.

13. The system of claim 1, wherein the portal is operably connected to a receptacle for receiving discharged fluids from the system.

14. The system of claim 13, wherein the system further includes a filter disposed between the portal and the receptacle for receiving discharged fluids from the system, said filter configured to render the discharged fluids safe for disposal in a sewer system.

15. The system of claim 1, wherein the chamber includes a spray nozzle associated with the portal.

16. The system of claim 1, wherein the system includes a lid which covers the chamber.

17. The system of claim 1, wherein the chamber is integrated within the clean zone of the hood.

18. The system of claim 1, wherein the system includes a computer processing unit.

19. The system of claim 18, wherein the computer processing unit is programmed to regulate flow of fluids into and out of the chamber.

20. The system of claim 18, wherein the computer processing unit is programmed to activate the ultrasonicator.

21. The system of claim 18, wherein the computer processing unit is programmable.

22. The system of claim 18, wherein the computer processing unit is programmed to monitor the fluids that enter the chamber to determine their disinfecting effectiveness.

23. The system of claim 1, wherein the system includes a dryer configured to accelerate the drying of the medical instruments after disinfection.

24. The system of claim 23, wherein the dryer is integrated into the chamber.

25. The system of claim 23, wherein the dryer is integrated within the hood and external to the chamber.

26. The system of claim 23, wherein the dryer includes a heater.

27. The system of claim 23, wherein the dryer includes a fan.

28. The system of claim 1, wherein the system further includes a power generator.

29. The system of claim 28, wherein the power generator is a solar cell.

30. The system of claim 28, wherein the power generator is a gas powered generator.

31. The system of claim 1, wherein the system is self-contained and is configured for transport and use without external connections.

32. The system of claim 1, wherein the system is configured to disinfect the medical instruments within a time period of 60 minutes or less.

33. The system of claim 1, wherein the portal is configured to cause fluids to enter and leave the chamber.

34. The system of claim 1, comprising multiple portals through which fluids enter or leave the chamber.

35. The system of claim 1, configured for sterilizing medical instruments.

36. The system for disinfecting medical instruments of claim 1,
wherein the fluid that is retained in the chamber is a disinfectant fluid comprising water, a colloidal transition metal, and a peroxygen;
wherein the disinfectant fluid enters or leaves the chamber through the portal; and
wherein the preparation area is adjacent to the chamber.

37. The system of claim 36, wherein the portal is operably connected to a source of a disinfectant fluid.

38. The system of claim 37, wherein the source of the disinfectant fluid is a disinfectant fluid tank.

39. The system of claim 37, wherein the source of disinfectant fluid includes a second disinfectant fluid.

40. The system of claim 39, wherein the second disinfectant fluid is an enzyme or detergent solution.

41. The system of claim 36, wherein the colloidal transition metal includes colloidal silver particles.

42. The system of claim 36, wherein the peroxygen includes a peroxide.

43. The system of claim 36, wherein the peroxygen includes a peroxide and a peracid.

44. The system of claim 36, wherein the portal is operably connected to a source of a rinse fluid.

45. The system of claim 44, wherein the rinse fluid is water.

46. The system of claim 36, wherein the portal is operably connected to a manifold configured to control inlet and outlet of fluids from the chamber.

47. The system of claim 36, wherein the portal is operably connected to a receptacle for receiving discharged fluids from the system.

48. The system of claim 47, wherein the system further includes a filter disposed between the portal and the receptacle for receiving discharged fluids from the system, said filter configured to render the discharged fluids safe for disposal in the sewer.

49. The system of claim 36, wherein the chamber includes a spray nozzle associated.

50. The system of claim 36, wherein the system includes a lid which covers the chamber.

51. The system of claim 36, wherein the system includes a computer processing unit.

52. The system of claim 51, wherein the computer processing unit is programmed to regulate flow of fluids into and out of the chamber.

53. The system of claim 51, wherein the computer processing unit is programmed to activate the ultrasonicator.

54. The system of claim 51, wherein the computer processing unit is programmable.

55. The system of claim 51, wherein the computer processing unit is programmed to monitor the fluids that enter the chamber to determine their disinfecting effectiveness.

56. The system of claim 36, wherein the system includes a dryer configured to accelerate the drying of the medical instruments after disinfection.

57. The system of claim 56, wherein the dryer is integrated into the chamber.

58. The system of claim 56, wherein the dryer is external to the chamber.

59. The system of claim 56, wherein the dryer includes a heater.

60. The system of claim 56, wherein the dryer includes a fan.

61. The system of claim 36, wherein the system further includes a power generator.

62. The system of claim 61, wherein the power generator is a solar cell.

63. The system of claim 61, wherein the power generator is a gas powered generator.

64. The system of claim 36, wherein the system is self-contained and is configured for transport and use without external connections.

65. The system of claim 36, wherein the system is configured to disinfect the medical instruments within a time period of 60 minutes or less.

66. The system of claim 36, wherein the portal is configured to cause fluids to enter and leave the chamber.

67. The system of claim 36, comprising multiple portals through which fluids enter or leave the chamber.

68. The system of claim 36, wherein the disinfectant fluid is a sterilant.

* * * * *